United States Patent
Olcott et al.

(10) Patent No.: US 7,777,191 B2
(45) Date of Patent: Aug. 17, 2010

(54) METHOD AND SYSTEM OF ADAPTIVE EXPOSURE FOR A CAMERA

(75) Inventors: Peter D. Olcott, Stanford, CA (US); Craig S. Levin, Palo Alto, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 112 days.

(21) Appl. No.: 11/584,370

(22) Filed: Oct. 20, 2006

(65) Prior Publication Data

US 2007/0152161 A1 Jul. 5, 2007

Related U.S. Application Data

(60) Provisional application No. 60/728,506, filed on Oct. 20, 2005.

(51) Int. Cl.
*G01T 1/166* (2006.01)
(52) U.S. Cl. ............... 250/363.07; 250/362; 348/208.4
(58) Field of Classification Search ............ 250/363.07, 250/362; 348/208.4
See application file for complete search history.

(56) References Cited

U.S. PATENT DOCUMENTS

| | | | |
|---|---|---|---|
| 6,441,848 B1 * | 8/2002 | Tull | 348/208.99 |
| 6,559,450 B1 * | 5/2003 | Berlad et al. | 250/363.07 |
| 6,723,988 B1 * | 4/2004 | Wainer | 250/336.1 |
| 6,778,210 B1 * | 8/2004 | Sugahara et al. | 348/208.4 |
| 2005/0010081 A1 * | 1/2005 | Doguchi et al. | 600/109 |
| 2005/0061952 A1 * | 3/2005 | Kawahara | 250/208.1 |

OTHER PUBLICATIONS

Barron, J.L., Fleet, D.J., and Beauchemin, S.S., "Performance of Optical Flow Techniques", 1994, pp. 1-60.
Simoncelli, E.P., "Bayesian Multi-Scale Differential Optical Flow", Handbook of Computer Vision and Applications, vol. 2, Chap. 14, Spring 1999, pp. 397-422.

* cited by examiner

*Primary Examiner*—David P Porta
*Assistant Examiner*—Jessica L Eley
(74) *Attorney, Agent, or Firm*—Greer, Burns & Crain Ltd.

(57) ABSTRACT

A method and/or device of adaptively controlling an exposure duration for a camera. A determination is made as to whether motion is present. If it is determined that motion is present, exposure duration for one or more images is automatically decreased. If it is determined that motion is not present, the frame exposure duration is automatically increased.

19 Claims, 7 Drawing Sheets

METHOD AND SYSTEM OF ADAPTIVE EXPOSURE FOR A CAMERA

PRIORITY CLAIM

This application claims the benefit of U.S. Provisional Patent Application Ser. No. 60/728,506, filed Oct. 20, 2005, under 35 U.S.C. §119.

BACKGROUND OF THE INVENTION

The present invention relates generally to the field of camera imaging. Embodiments of the present invention relate more specifically to the fields of gamma camera imaging, handheld cameras, and surgical imaging.

A handheld gamma ray camera is a nuclear medicine device used for close proximity imaging of radioactively labeled tracers that are injected into the body. An exemplary application of such a camera is surgical cancer staging.

Cancer staging is a process where tests are performed to determine, after a primary tumor has been diagnosed, if cancer cells have spread locally or throughout the body. Staging of breast cancers and melanoma often requires lymphatic dissection and pathology. A technique called a sentinel node (SN) procedure attempts to locate the "sentinel" lymph node, or the closest lymph node of the lymphatic system that directly drains the tumor basin. In this procedure, just that one sentinel node is located and removed. This process is an alternate procedure to conventional lymph node dissection that reduces the invasiveness and complications of the surgical biopsy procedure. The sentinel lymph node is a good indicator of cancer invasiveness; if the sentinel node is clear of cancer cells then it is unlikely that the cancer is actively spreading.

In an exemplary surgical cancer staging procedure, illustrated in FIG. 1, a surgeon injects a radioactive substance (a tracer) 10, a blue dye, or both into the area around a primary tumor site 12. An exemplary tracer is radioactive Tc-99 m Sulfur Colloid, having a large particle size (appr.100-500 nm). Lymphatic vessels 14 carry the tracer 10 to the first lymph node (sentinel node) 16 into which the area drains; this is the lymph node most likely to contain cancer cells. This procedure helps to "map" the drainage pattern of lymphatic fluid from the skin to the lymph nodes. Such a map may help to show the direction the cancer is likely to spread and the lymph node most likely to contain cancer cells. The surgeon can either visually identify the blue dye or detect the tracer 10 by detecting the presence of radiation from the tracer. The lymph node 16 can then be removed for examination under a microscope (pathology).

One method of detecting the tracer 10 uses non-imaging intra-operative gamma detecting probes, which produce a sound proportional to counts that are detected near a tip of the probe. However, because the tracer distribution is heavily concentrated at the injection site, and only a few percent typically ever drains into the lymph nodes, a non-imaging probe can be easily confused by the injection site, and significant training and experience are needed to avoid this complication.

Another method of tracer detection uses a gamma ray camera, such as a fixed or handheld gamma ray camera. As opposed to the non-imaging probes, a handheld gamma ray camera can help the localization of lymph nodes, because it can give a surgeon real-time visual cues as to tracer distribution relative to the injection site. However, problems arise with the use of handheld gamma ray cameras that may result in poor images or complex operation.

For example, handheld gamma ray cameras suffer from low statistical quality image data. In gamma ray imaging, tracer quantities of the radioactive substance and relatively low photon count sensitivity of gamma ray collimators may mean only a few counts are collected by the imaging surface of the detector. Additionally, blurring artifacts can result when the gamma ray camera is scanned across the field of interest. For instance, hand-motion of the gamma ray camera during use (e.g., during a surgical biopsy procedure) will blur active objects within the field of view.

There are competing technologies that attempt to solve problems associated with a moving gamma ray camera. One general solution uses motion detectors to synthesize a large field of view. An exemplary method attempts to perform tomography by tracking the spatial location (derived by absolute motion and position sensor) of the gamma ray camera, forming limited angle projections, and then backprojecting these into some form of tomographic image or planar tiled image. This technique, however, has significant limitations in the reconstructed resolution of the system (e.g., often >10 mm). Slight misidentification of the absolute position and rotation of the camera typically results in large blurring effects and streaks on the reconstructed image.

In another compensation method, blurring artifacts may be removed by manual intervention by selectively clearing a current acquisition frame, such as by operating a pedal while manipulating the camera. However, such an operation can be burdensome for the camera operator, and in many cases will require a separate person. For example, a known practice uses a dedicated technician who controls the acquisition. The surgeon must give verbal commands to the technician to clear the current frame.

As another alternative, a fixed high frame rate may be used to reduce motion-blurring artifacts. However, in this case, many events are thrown away and poor statistical quality images are formed from the relatively few events that are captured.

Thus, known compensation methods insufficiently address the above-described problems. Such problems have resulted in continued use of non-imaging probes for surgical cancer staging, in spite of the benefits of gamma cameras.

SUMMARY OF THE INVENTION

Embodiments of the instant invention provide a method and/or device of adaptively controlling an exposure duration for a camera. Generally, in a preferred method, a determination is made as to whether motion is present. If it is determined that motion is present, exposure duration for one or more images is automatically decreased. If it is determined that motion is not present, the exposure duration is automatically increased. Cameras embodying preferred methods are also provided.

DETAILED DESCRIPTION

Preferred embodiments of the present invention provide methods and devices to adjust the exposure duration of a camera such as, but not limited to, a handheld gamma ray camera automatically to allow automatic control over imaging characteristics. Automatic controls of camera parameters in a handheld gamma ray camera, for example, allow a surgeon to focus on locating a sentinel node without the burden of manually adjusting many parameters (e.g., exposure duration) to get a usable image.

Generally, a determination is made as to whether motion is present. Such motion, for example, may be due to movement of the camera, movement of the imaged object, or both. Based on this determination, the exposure duration for one or more images is dynamically adapted to limit the effects of motion, preferably without lowering the statistical quality of image data. As used herein, "exposure duration" refers to how long counts are accumulated in a particular frame before the frame is cleared or displayed to a user. In a preferred method, when motion is detected, the exposure duration is automatically decreased, allowing fewer counts per frame. When motion is not detected, the exposure duration is automatically increased, allowing more counts per frame.

Preferred embodiments of the present invention use acquired image data itself to detect motion. In this way, hardware motion detection equipment can be reduced or eliminated. Additionally, because the acquired image data is affected by movement of the camera and the imaged object, using the image data can account for both sources of motion between images.

According to exemplary embodiments of the present invention, a camera is provided that is configured for an adaptive exposure duration control method. According to particular exemplary embodiments, an intra-operative hand-held gamma ray camera is provided to image sentinel lymph nodes or for other applications. The camera is configured via software, firmware, and/or hardware to provide an adaptive exposure control method.

Figure 1:
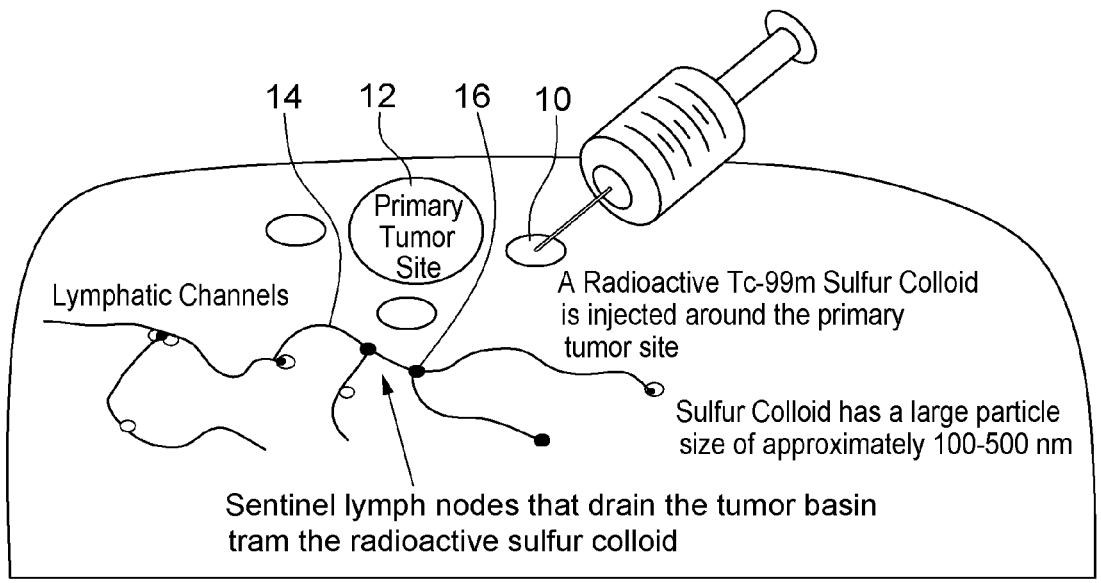
FIG. 1 schematically shows a conventional detection method for sentinel nodes.
Figure 2A:
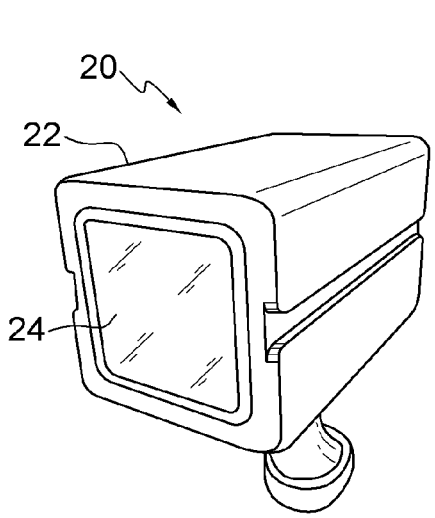
FIGS. 2A and 2B are perspective views of a handheld gamma ray camera according to an exemplary embodiment of the present invention.
Figure 2B:
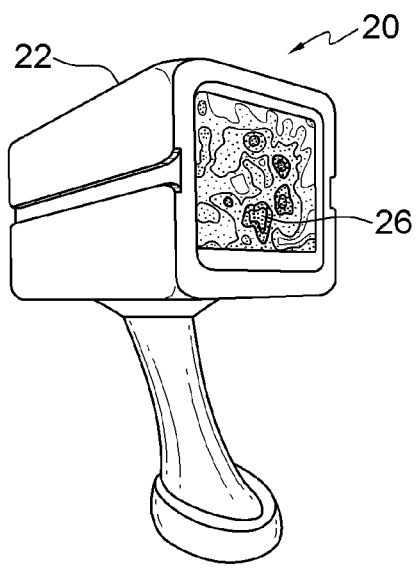

Referring now to the drawings, FIGS. 2A and 2B show a camera 20, which in FIGS. 2A-2B is embodied in a gamma camera such as a scintillation-based gamma camera, according to an exemplary embodiment of the present invention. Generally, the camera may be any camera that records signals from a source one wishes to track, and the present invention is not intended to be limited to gamma cameras.

A housing 22 generally encloses the camera 20, and includes a handle for easier manipulation of the camera. A window 24 exposes an image detector within the camera 20, which is directed towards an energy source (such as, but not limited to, the tracer 10). A suitable power supply (not shown) provides power to the camera, and an actuator may be provided to allow the camera to acquire image data selectively. A display or monitor 26 may be provided within the housing 22 for viewing an image generated from the camera 20. Alternatively or additionally, an external display or monitor may be suitably coupled to the camera 20 for viewing. A suitable storage device (not shown) may be provided to store data and/or generated images.

Figure 3:
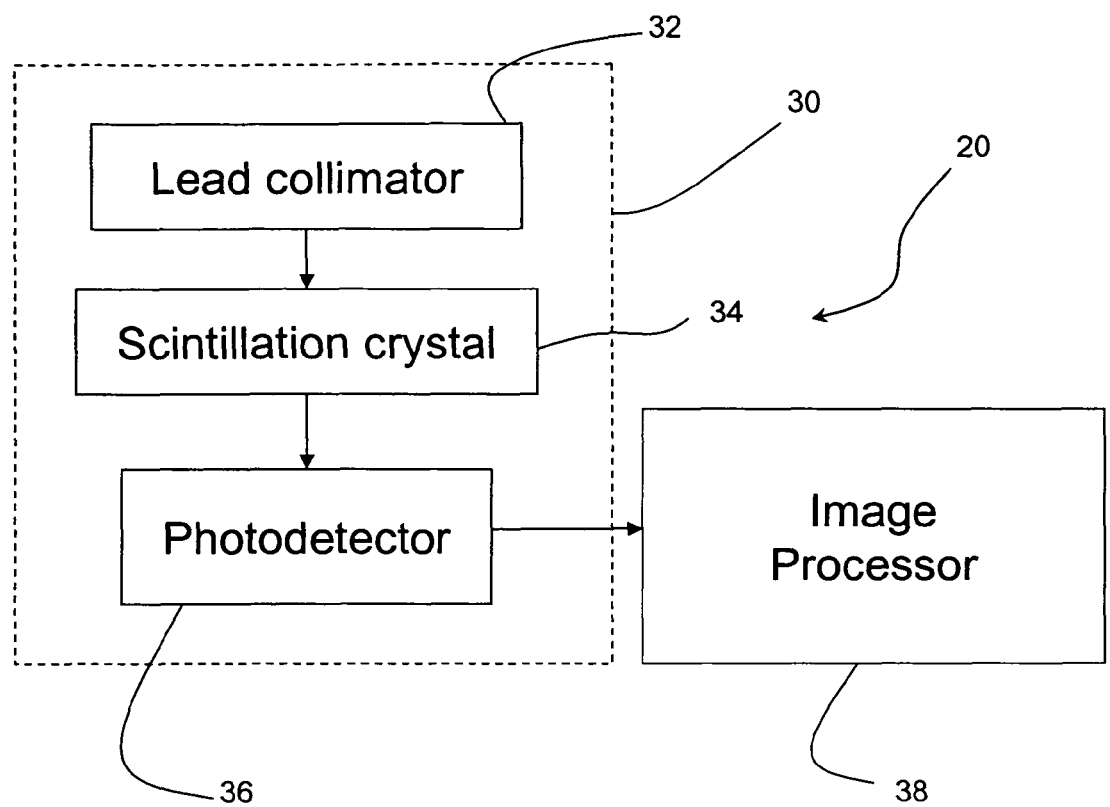
FIG. 3 is a block diagram showing components of an exemplary gamma ray camera, according to an embodiment of the present invention.

As shown in FIG. 3, to provide an image, the camera 20 includes an image detector 30 contained within the housing 12. Generally, the image detector 30 provides image data (e.g., a position sensitive signal) based on a received energy or radiation source, such as, but not limited to, gamma rays, infrared light, visible light, or other energy sources, that allows an image to be acquired.

In the exemplary camera 20 shown in FIG. 3, the exemplary image detector 30 provides image data based on gamma rays. The exemplary image detector 30 includes a lead collimator 32, such as a parallel hole or pinhole, to directionally filter the gamma rays. An exemplary lead collimator 32 is a hexagonal parallel hole collimator with 1.3 mm hole size and 0.2 mm septa. A scintillation crystal 34, such as a pixellated or sheet crystal, is coupled to the lead collimator 32 to detect the gamma rays by interacting with the gamma rays and producing a flash of light. An exemplary scintillation crystal 34 is 29×29 pixellated 1.5×1.5×6 $mm^3$ NaI(Tl) crystal. A spatially sensitive photodetector 36, such as silicon photodiodes or a position sensitive photomultiplier tube, receives the flashes of light, and generates an event representing a gamma ray interaction. An exemplary photodetector 36 is a flat panel multi-anode Hammatsu H8500 Position Sensitive Photomultiplier, read out using a Symmetric Charge Division PCB circuit. The events from the image detection device 30 are processed by a processor 38 to provide counts, which form image data. The processor 38 may be incorporated within the housing 12, or may be external to the housing, such as, but not limited to, a computer.

Examples of lead collimators 32, scintillation crystals 34, spatially sensitive photodetectors 36, and processors 38 for scintillation-based gamma ray cameras are known to those of ordinary skill in the art, and thus a detailed description of these components is omitted herein. Non-limiting examples are provided in Olcott, P. D.; Talcott, J. A.; Levin, C. S.; Habte, F.; Foudray, A. M. K., "Compact readout electronics for position sensitive photomultiplier tubes", Nuclear Science, IEEE Transactions on, Volume 52, Issue 1, Part 1, Febuary 2005 Page(s):21-27, and Olcott, P. D.; Habte, F.; Levin, C. S.; Foudray, A. M., "Characterization of performance of a miniature, high sensitivity gamma ray camera", Nuclear Science Symposium Conference Record, 2004 IEEE, Volume 6, 16-22 Oct. 2004 Page(s):3997-4000.

It will also be appreciated that the image detector 30 may instead use, for example, an all-semiconductor based imaging system, a cadmium zinc telluride imaging system, or other gamma ray radioactive detectors in place of the scintillation crystal 34 and photodetector 36 for gamma ray radiation detection. Other apparatuses, such as, but not limited to, semiconductor detectors, etc., may provide an image detector in place of image detector 30 for detecting other sources of energy, as will be appreciated by one of ordinary skill in the art.

Preferred methods of the present invention may be performed, for example, by a suitable image processor 38 such as, but not limited to, software, hardware, or firmware for the camera 20 (either within the camera itself, or in communication with the camera). Exemplary hardware or firmware, for example, may be embedded within the processor 38 to cause the processor to perform one or more of the inventive methods. Exemplary software, accessible via any suitable device or method, also may configure operation of the processor 38 to cause the processor to perform one or more of the inventive methods. Embodiments of the present invention may also be embodied in a camera such as, but not limited to, the camera 20, or a conventional or to-be-designed camera, including but not limited to a handheld gamma camera, having image processing capabilities that is configured via software, hardware, or firmware to perform one or more of the inventive methods.

Figure 4:
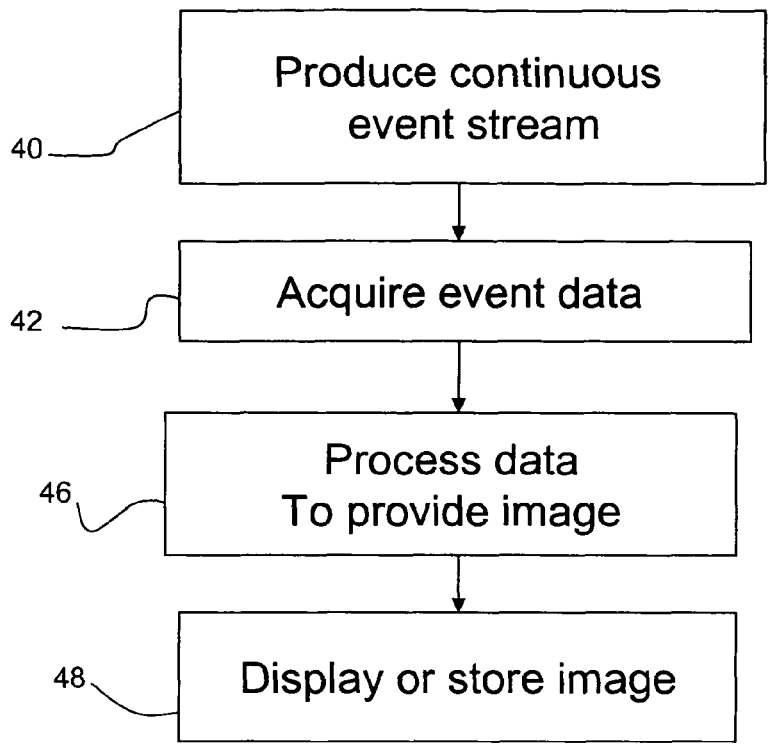
FIG. 4 is a flow chart showing steps in an exemplary image detection method, according to embodiments of the present invention.

Referring now to FIG. 4, showing an exemplary operation, as will be appreciated by one of ordinary skill in the art, an event stream 40 is produced. Most gamma cameras, such as the exemplary handheld gamma ray camera 20, produce a continuous scintillation event stream, which includes the location of the event (an interaction, such as a single gamma ray interaction with the scintillation crystal) on the photodetector, and the energy of the interaction. An event is processed to provide a count, which may refer, for example, to one quanta of signal that is localized in space and time to a detector pixel.

The continuous event stream is Poisson distributed in arrival time. For example, tens or hundreds of events may be collected to go into a single frame that is presented to a user. In contrast, an image detector for an optical camera such as a charge-coupled device (CCD) integrates all charge into a discrete fixed frame. The processor uses software or firmware to convert the events, such as the continuous event stream of the gamma camera, into an image for display, and to improve the image quality through suitable image processing techniques.

In a typical gamma camera, for example, data may be acquired 42, such as from the photodetector 36, and processed 46 to provide an image, which then may be stored and/or displayed 48 on the display 26. Image processing may include, for example, intensity scaling and spatial filtering, the output of which typically is an image for storage and/or display.

Figure 5:
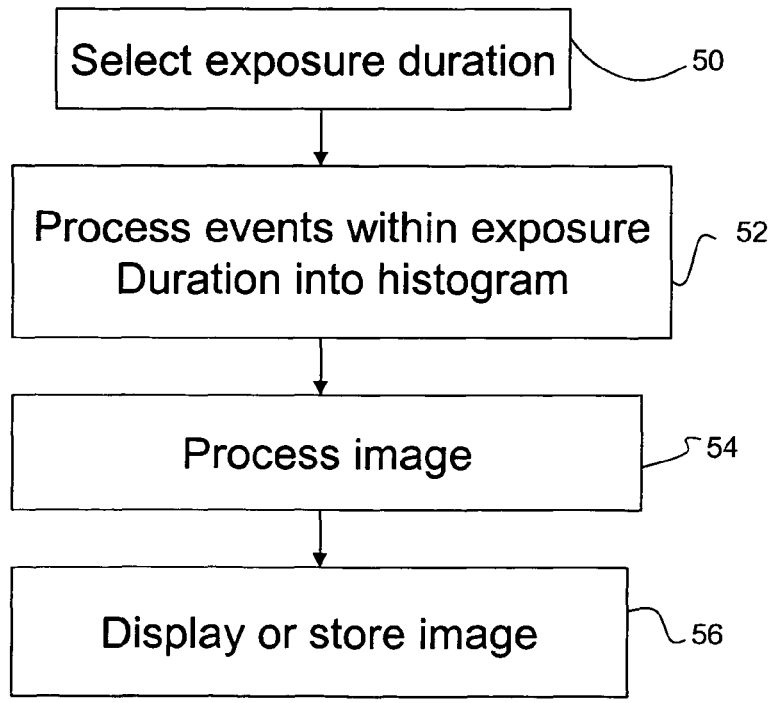
FIG. 5 is a flow chart showing steps in a process to convert a continuous stream of events into an image, according to embodiments of the present invention.

Referring now to FIG. 5, showing an exemplary process to convert a continuous stream of events into visual information, exposure duration, such as a finite acquisition window or acquisition time window, is selected 50 for acquiring image data. There are various ways to select the exposure duration. The exposure duration can be manually determined per frame; for example, the acquisition may be started and stopped, or the current frame may be reset. Alternatively, a time window can be fixed, and the image updated at a given frame rate. In still other cases, the window can be left open, and all image counts may be allowed to accumulate continuously. In the latter case, the system will continuously update as events are detected.

Given the selected exposure duration, all events in the acquisition window or acquisition time window are processed 52 into a histogram to form the image. This image undergoes basic image processing 54, including smoothing (non-linear or Gaussian spatial filtering) and/or assigning the values in each bin a value either based on color or intensity (intensity scaling). The image is stored and/or displayed 56 to the user as a function of time. A series of frames can also undergo temporal filtering, and then displayed to the user.

Because the event stream is continuous and Poisson distributed in arrival time, the longer a gamma ray camera such as the camera 20 is held in a particular position, the better the image quality. Often, gamma rays are taken by a gamma ray camera from non-moving image objects, for example when both a camera and a patient are not moving. However, this often is not desirable or possible with usage of a portable (e.g., handheld) gamma ray camera, such as when the camera is used for surgical cancer staging.

Therefore, it is advantageous to produce an optimal or at least improved image while the camera 20 or imaged object is moving. One way of improving image quality is by adjusting the exposure duration for acquiring image data (step 50). There are also special considerations with gamma cameras as opposed to other types of cameras such as optical cameras. When an optical camera or imaged object is moved, an image blurs, and a higher frame rate can be used to improve or optimize image quality. However, with a gamma ray camera, due to the low event rate, if the frame rate is made too high (i.e. the exposure duration is too low), the number of events for a particular window or windows may be too limited to provide a useful image.

One method of addressing this is to manipulate the camera 20 and manually control the exposure duration, for example using a pedal to select the end of a particular frame and control data acquisition. However, it will be appreciated that such an operation may be burdensome for a camera operator, and in many cases will require a separate person to control the exposure duration. For example, a dedicated technician may control data acquisition. The surgeon must give verbal commands to the technician to clear the current frame. This method is highly undesirable, and accordingly the use of handheld gamma ray cameras has not been as widespread as it should be given the other advantages of gamma ray cameras as compared to non-imaging intra-operative probes.

Thus, methods are provided according to embodiments of the present invention to adjust exposure duration of a camera automatically, including, but not limited to, a gamma camera such as the handheld gamma camera 20. Automatic adjustment of exposure duration avoids the problems associated with manual exposure duration adjustment, while providing usable images.

Exemplary methods can operate given the continuous stream of events that are acquired with a position and energy sensitive scintillation camera. Because the exemplary camera 20 is hand-held, it cannot be assumed that the continuous stream of events will be imaging the same area. The continuous stream of events is displayed as a series of discrete image frames to the user. It will be appreciated, though, that methods and devices according to embodiments of the present invention may also be used with discrete fixed frames, such as with optical cameras.

Figure 6:
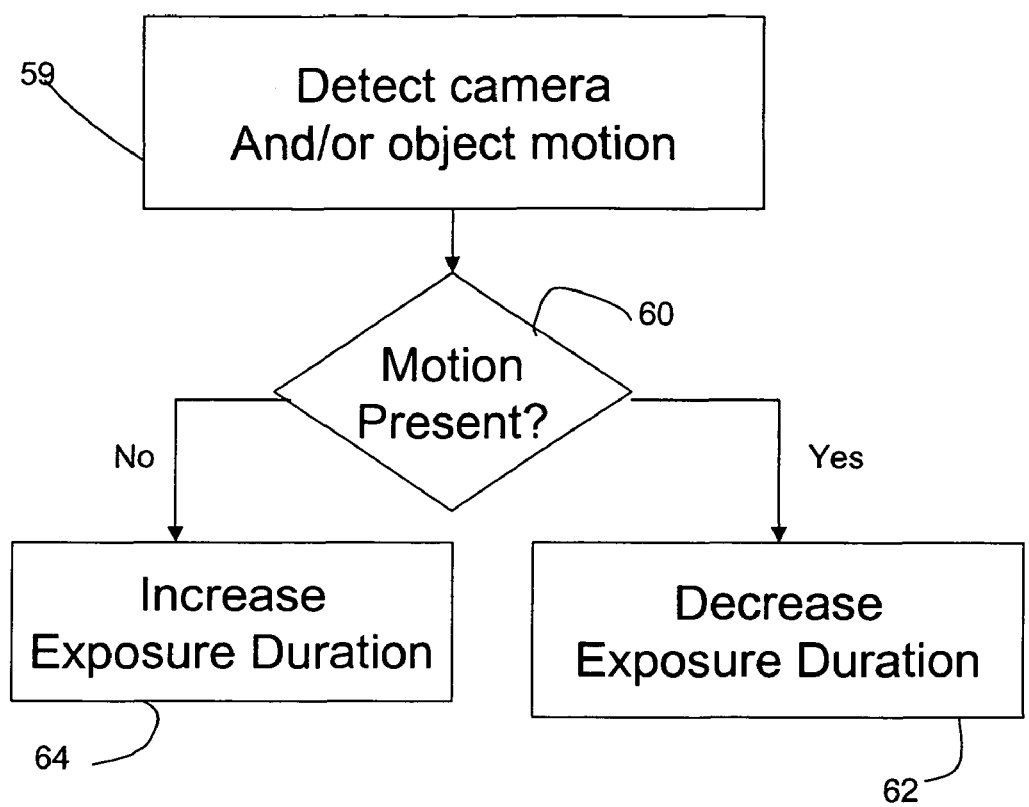
FIG. 6 is a flow chart showing steps in an exposure duration control method, according to embodiments of the present invention.

Referring now to FIG. 6, showing a preferred method for adjusting exposure duration, motion is detected 59 using hardware motion detection and/or acquired image data. A determination then is made 60 as to whether motion is present, for example by comparing the detected motion to a threshold. Based on this determination, the exposure duration is automatically adjusted accordingly. For example, if motion is detected (e.g. a Boolean "yes"), the exposure duration is reduced 62 to limit blurring. If motion is not detected (e.g., a Boolean "no"), the exposure duration is increased 64 to improve the image.

The camera and/or object motion can be detected 59, for example, by a motion detector(s), such as but not limited to an accelerometer(s). For example, an accelerometer output may be compared to a predetermined threshold to make the determination.

Alternatively or additionally, a preferred method of motion determination uses the acquired image data itself to determine whether motion is present. "Motion" as used herein refers to a sufficient amount of relative movement between the camera 20 and the object to cause blurring of the image. For example, if the camera 20 and/or the object move relative to each other such that the produced image will shift or blur by more than half the resolution of the camera 20 in a particular exposure duration, motion is considered present. This is because camera motion and object motion act in combination to cause image blurring. In some preferred embodiments, the acquired image data is used to determine correlated motion. Correlated motion is defined over a region of time, and can be calculated from, as a non-limiting example, the correlated change of pixel intensity over a period of time.

As one non-limiting example, sufficient correlated motion may be determined using an average of flow vectors, though various other statistical tests may be used, as will be appreciated by those of ordinary skill in the art. Correlated motion may be determined in a single frame, and/or may be considered in view of motion in previous frames. In a preferred embodiment, flow vectors are determined by using the acquired image data as inputs for an optical flow algorithm. This can be used to determine whether the camera or imaged object is moving. Using the acquired image data can avoid the use of external motion detectors, though it can also be used in combination with motion detectors. Further, a correlated motion determination method is preferred when both the camera 20 and the object to be imaged is moving.

In a preferred motion determination method using acquired image data, given frames as a function of time (i.e., histogrammed events), the Lucas-Kanade optical flow constraint equation is solved to derive a velocity vector for each pixel from a smoothed sequence of short frames. There are several advantages to using optical flow in this way. For example, with gamma ray cameras, it can be very difficult to detect motion in the continuous stream of events with very low statistics, which is a problem inherent to nuclear medicine. Determination of movement has to be made with extremely low statistics, usually only 5-10 counts in an entire image. Using purely the magnitude of the temporal gradient is far too noisy to determine motion accurately.

The correlated motion provided by the optical flow constraint equation gives a much higher signal-to-noise method than the magnitude of the change in intensity of the pixels as a function of time. Optical flow typically has been used for removing blurring artifacts or detection of motion of a single object in a sequence of video frames. As used in preferred embodiments of the present invention, however, optical flow provides a very robust method to determine if motion in an entire sequence of sequential frames is occurring, and this information can be used to set the exposure duration.

The Lucas-Kanade optical flow constraint equation (e.g., see Lucas and Kanade, "An iterative image registration technique with an application to stereo vision," Proc. DARPA Image Understanding Workshop, 1981, pp. 121-130) assumes that the intensity is constant over motion that involves translation and rotation over small distances.

$$(\nabla E)^T \cdot \vec{v} + \frac{\partial E}{\partial T} = \vec{0} \quad (1)$$

$$\vec{v} = -(\nabla E^T \cdot \nabla E)^{-1} \cdot (\nabla E)^T \cdot \frac{\partial E}{\partial t} \quad (2)$$

With this assumption (1), one can solve for the velocity vector (2) for each pixel centered over a small neighborhood, or over the entire camera field (if the entire field is moving).

Alternatively, any suitable method, known or to-be-known, that calculates per pixel or neighborhood of pixel motion between a sequence of individual events or events collected into frames could be used to determine correlated motion of the camera. Further, camera motion and/or object motion can be calculated by simple temporal gradient methods (magnitude of difference between frames in time) that do not sense correlated motion. However, preferred embodiments determine correlated motion. Other nonlimiting optical flow methods may be found in, for example, J. L. Barron, D. J. Fleet, and S. S. Beauchemin, "Performance of Optical Flow Techniques", IJCV 12:1, pp. 43-77, 1994; and Eero P. Simoncelli, "Bayesian Multi-Scale Differential Optical Flow", Handbook of Computer Vision and Applications, vol. 2, chapter 14, pages 297-422, Academic Press, Spring 1999.

Figure 7:
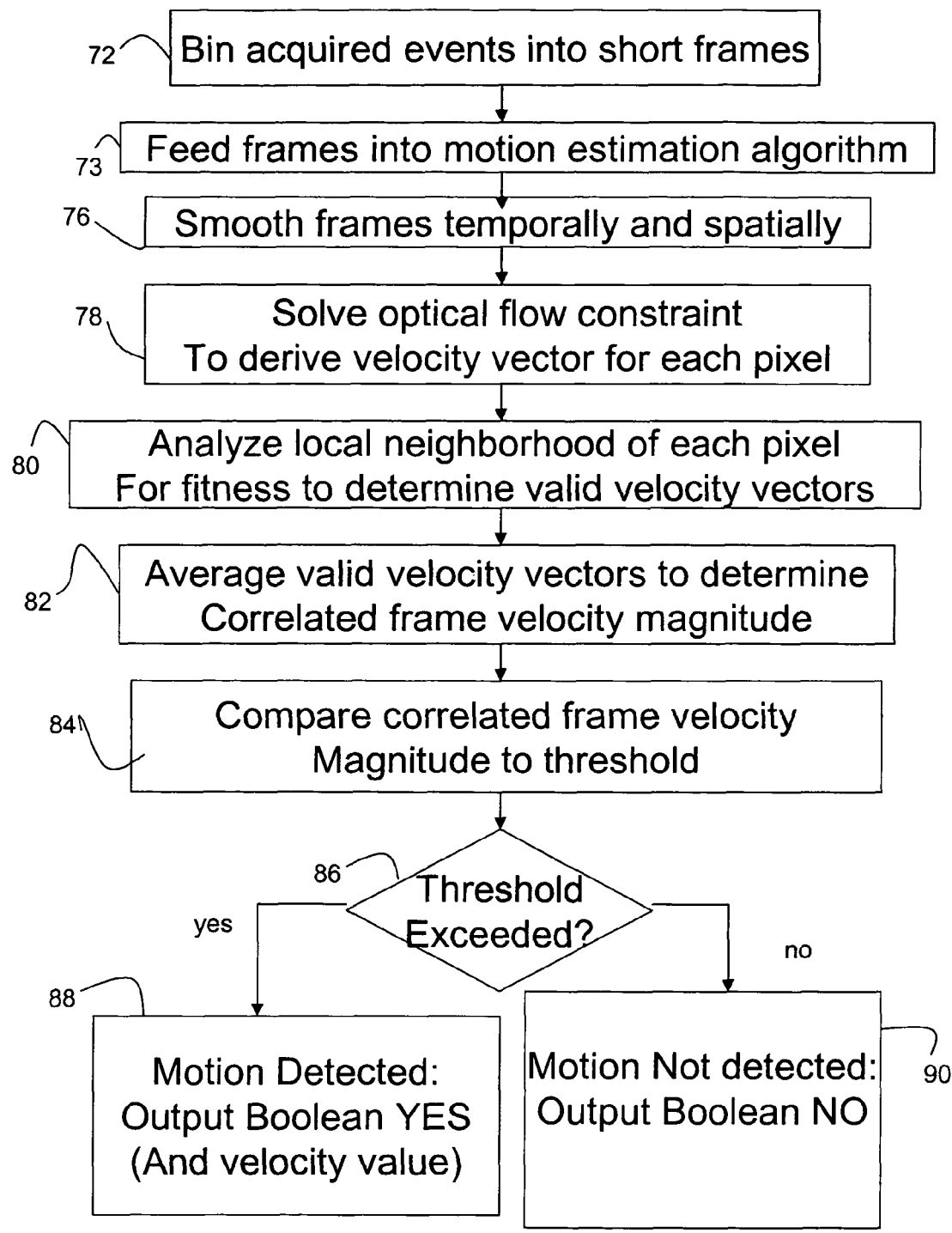
FIG. 7 is a flow chart showing steps in an exposure control method using an optical flow algorithm, according to preferred embodiments of the present invention.
Figure 8:
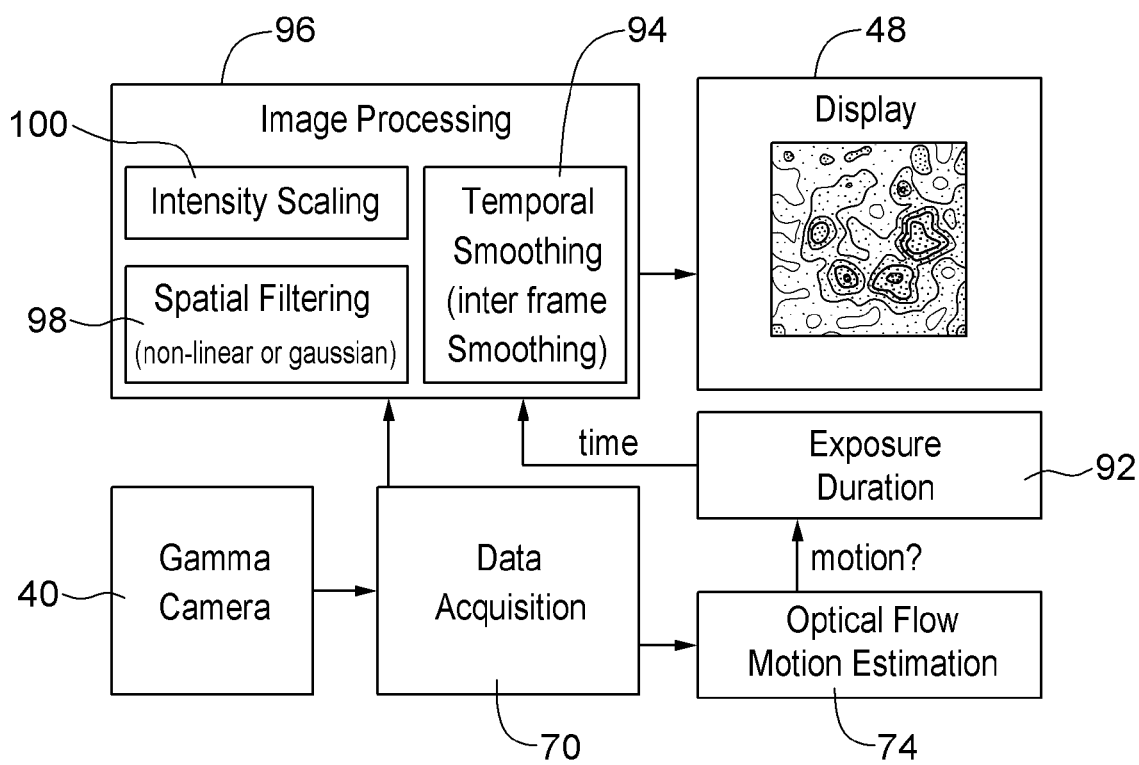
FIG. 8 is a functional block diagram showing steps in an exemplary motion estimation algorithm, according to embodiments of the present invention.

FIGS. 7-8 show an exemplary exposure control method using an optical flow algorithm. As part of data acquisition 70, the events are binned 72 into very short (as a nonlimiting example, 0.5 second) frames to detect motion and fed 73 into a motion estimation algorithm 74, such as an optical flow algorithm. The very short frames preferably are of the fastest exposure duration that is known a priori that will work for the imaging protocol currently performed. It preferably is fixed for the current imaging task. In an exemplary motion estimation algorithm 74, the frames are smoothed 76, for example temporally by a 3-frame Gaussian filter, and then spatially by a 3×3 Gaussian filter, to reduce noise. Events are detected on the camera according to a Poisson distribution. The variance in intensity of each pixel is proportional to the inverse mean number of counts detected in that pixel for a given fixed frame size. The more counts detected per pixel, the lower the variance in intensity of the pixel. By binning the events to very short frames, there are a low mean number of counts detected per pixel, causing a significant variance in the intensity of each pixel. The preferred optical flow algorithm uses spatial and temporal gradients to smooth out the variance, because gradient operations are sensitive to noise. Gaussian filtering is performed on the short frames to improve the calculation of the gradient in both space and time.

The optical flow constraint, such as the Lucas-Kanade optical flow constraint equation above, is solved, and a velocity vector is derived 78 for each pixel. Next, based on the determined velocity vector for each pixel, it is determined whether correlated motion is detected between sequential frames. Particularly, the local neighborhood of each pixel is analyzed 80 for its fitness for determining if a valid velocity vector is present. In a preferred method, the ratio of eigen values of the covariance matrix of the spatial gradients is compared to a window of values. If the ratio of the eigen values is too large or too small, then the region around the pixel is not fit to solve for a velocity vector. Vectors that are fit are then averaged 82 and the correlated frame velocity magnitude (e.g., pixels/second) is compared to a threshold 84, and a determination is made 86 as to whether the threshold is exceeded (or met). An exemplary threshold, for example, may be predetermined or based on data acquisition when non-motion is known.

Figure 9:
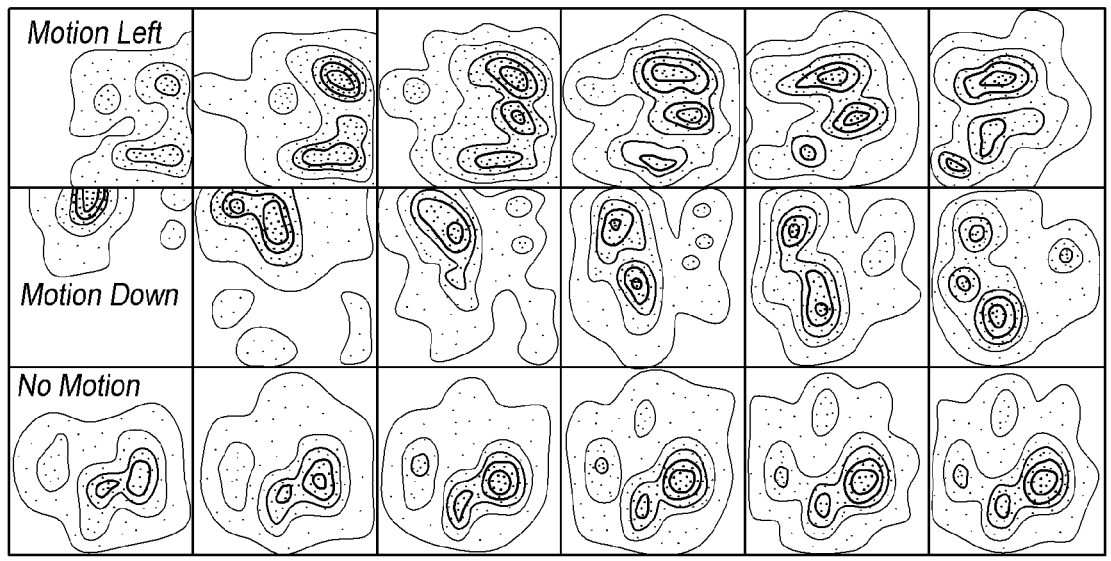
FIG. 9 shows separate frame video sequences with calculated optical fields.
Figure 10:
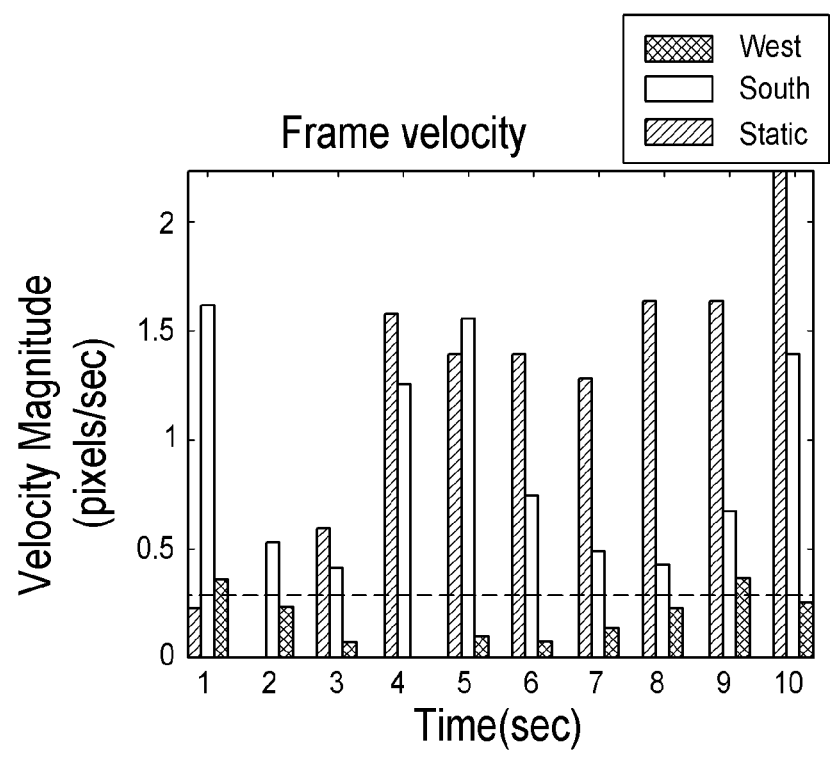
FIG. 10 shows correlated frame velocity calculated from the three separate video sequences shown in FIG. 9.

If the magnitude exceeds (or meets) the threshold, it is determined that correlated motion between sequential frames exists 88; otherwise, it is determined that correlated motion between sequential frames does not exist 90. An output of the motion algorithm, for example, may be a Boolean variable or a Boolean and a value proportional to the detected velocity. Alternatively, a value proportional to the detected velocity may be output without a Boolean variable. FIG. 9 shows an example of three separate frame video sequences (left, down, and no-motion) taken with a handheld gamma camera with calculated optical flow fields. In the case where no motion is present, the optical flow fields show very little correlated motion as compared with motion left and motion down. FIG. 10 shows correlated frame velocity calculated from the three separate video sequences shown in FIG. 9. As shown, optical flow provides a robust determination of velocity even when there are extremely low statistics. The dotted line in FIG. 10 shows an exemplary velocity threshold (e.g., 0.25 pixels/second) used to determine that motion is present. If a frame crosses this threshold, the motion is detected for a frame. In FIG. 10, two of the motion sequences shown, west and south, cross the velocity threshold over a ten-second acquisition, while non-motion is reliably detected in the static sequence.

If motion detection based on the image data and other motion detector methods are used together, the results of each may be combined for a final determination as to motion. For example, the Boolean results from each method may be inputs to an AND function, and these inputs may be appropriately weighted.

Referring again to FIGS. 6 and 8, the exposure duration is adapted 92 based on the outcome of the optical flow motion estimation algorithm 74. For example, if correlated motion is detected between sequential frames, the frame exposure duration is automatically decreased 64 (see FIG. 6). If no motion is detected, it is automatically increased 62, and the image counts accumulate. The determined exposure duration (e.g., a time) preferably is input to a temporal (inter frame) smoothing or filtering algorithm 94 that, along with the other image processing 96 that may be used, provides an image within a particular time window for display and/or storage. The temporal smoothing or filtering may be box filtering or Gaussian filtering, with a width of the Gaussian or box filter proportional to the determined exposure duration. Additional image processing steps may include but are not limited to image resizing to improve image resolution (spatial filtering 98), compression of image intensity (intensity scaling 100) to bring out small weak features in images, etc. The processed image may then be displayed 48.

In certain embodiments, the exposure duration can increase or decrease by a fixed amount (averaging). Alternatively, the exposure duration can be decreased by an amount proportional to the detected velocity, but increased by a fixed amount. As another (and preferred) alternative, a peak detection method, exposure duration may be decreased by a larger amount than the increase if motion is detected, thus quickly converting to a fast frame rate, and slowly recovering. These latter methods provide the advantage of making the camera 20 more responsive, but provide the disadvantage of shorter exposures on average.

According to the peak detection method, if a user, for example, is scanning to locate the sentinel node 16 or some other focus of radio-tracer, the exposure duration is automatically made very short, and the gamma camera 20 will be responsive with little blurring. If the user finds some active structure of interest while scanning, the user will stay fixed over the target. In this case, the exposure duration is automatically made higher, and a large number of counts will be collected. The user will see an image that contains less statistical noise than if short exposure duration was used and significantly less blurring than if the image was acquired during scanning motion.

Methods and devices for imaging, image processing, and controlling exposure duration according to embodiments of the present invention have been shown and described, having certain features and advantages. By providing automatic exposure duration control, a separate nuclear medicine technician is not needed to control exposure duration during a surgical cancer staging procedure. Additionally, in contrast to the technique of synthesizing a large field of view using motion detectors, an exemplary camera 20 according to embodiments of the present invention can provide improved spatial resolution (e.g., 2 mm-5 mm), with motion being directly determined from the image data.

Though the description herein focuses generally on gamma ray cameras, and especially handheld gamma ray cameras, it will be appreciated, as mentioned above, that aspects of the present invention will be applicable to other types of cameras or optical microscopic imaging devices to correct camera motion artifacts. The image detector, accordingly, may be configured to receive any of various different energy types, and/or detect energy types in any of various ways. For example, an optical camera having an image detector including a lens and CCD and a processor may be configured to adjust exposure duration based on the result of motion detection (e.g., using hardware motion detection and/or a processor configured to determine motion from acquired image data). As a nonlimiting example, this method may have benefits, for example, in low-light level CCD video imaging. Embodiments of the present invention may be useful in other nuclear imaging technologies, particularly (but not necessarily) if the imaging task has low statistical image quality and a moving imaging device or moving target. For example, this technique may be applied to real time imaging radioactive sources for weapon proliferation monitoring. An example of such real time imaging is described in, e.g., Klimenko, A. V.; Priedhorsky, W. C.; Hengartner, N. W.; Borozdin, K. N., "Efficient strategies for low-statistics nuclear searches", Nuclear Science, IEEE Transactions on, Volume 53, Issue 3, Part 3, June 2006 Page(s):1435-1442.

While various embodiments of the present invention have been shown and described, it should be understood that other modifications, substitutions, and alternatives are apparent to one of ordinary skill in the art. Such modifications, substitutions, and alternatives can be made without departing from the spirit and scope of the invention, which should be determined from the appended claims.

Various features of the invention are set forth in the appended claims.

What is claimed is:

1. For a gamma camera including an image detector receiving events to provide pixels in a two-dimensional imaging surface, a method for adaptively controlling an exposure duration of one or more images, the method comprising:
   determining whether motion exists; and
   based on said determining, increasing or decreasing the exposure duration;
   wherein said detecting comprises:
      obtaining a plurality of sequential frames having a time duration shorter than the image exposure duration; and
      determining whether motion is present between two or more of the sequential frames;
   wherein said increasing or decreasing the exposure duration comprises:

if motion between sequential frames is determined, decreasing the exposure duration by a first fixed amount; and if motion between sequential frames is not determined, increasing the exposure duration by a second fixed amount;

wherein said first fixed amount is greater than said second fixed amount.

2. The method of claim 1, wherein said determining comprises:
acquiring image data;
determining motion using said acquired image data.

3. The method of claim 1, wherein said determining whether motion is present between two or more of the sequential frames comprises:
deriving a velocity vector for each of a plurality of pixels in the two or more sequential frames;
based on said derived velocity vectors, determining a correlated frame velocity magnitude.

4. The method of claim 3, further comprising:
comparing said correlated frame velocity magnitude to a threshold.

5. The method of claim 3, wherein said deriving a velocity vector comprises solving an optical flow constraint for each of a plurality of pixels in the two or more sequential frames.

6. The method of claim 5, further comprising:
before said determining a correlated frame velocity magnitude, selecting a plurality of valid velocity vectors from among said derived velocity vectors;
wherein said selecting comprises analyzing a local neighborhood of each of the plurality of pixels for fitness;
wherein said determining a correlated frame velocity magnitude is based on said selected plurality of valid velocity vectors.

7. The method of claim 3, further comprising:
before said deriving a velocity vector, at least one of spatially and temporally smoothing said obtained plurality of sequential frames.

8. The method of claim 1, wherein said increasing or decreasing the exposure duration further comprises:
temporally smoothing said obtained plurality of sequential frames based on one of said increased exposure duration and said decreased exposure duration.

9. The method of claim 1, wherein the received events comprise a continuous event stream.

10. The method of claim 1, wherein the received events are Poisson distributed in arrival time.

11. For a gamma camera including an image detector receiving events to provide pixels in a two-dimensional imaging surface, a method for adaptively controlling an exposure duration of one or more images, the method comprising:
determining whether motion exists; and
based on said determining, increasing or decreasing the exposure duration;
wherein said detecting comprises:
obtaining a plurality of sequential frames having a time duration shorter than the image exposure duration; and
determining whether motion is present between two or more of the sequential frames;
wherein said increasing or decreasing the exposure duration comprises:
if motion between sequential frames is determined, decreasing the exposure duration by at least one of a fixed amount and an amount proportional to an amount of image motion; and if motion between sequential frames is not determined, increasing the exposure duration by at least one of a fixed amount and an amount inversely proportional to an amount of image motion.

12. The method of claim 11, wherein said determining comprises:
determining camera motion using a hardware motion detector coupled to the camera.

13. An imaging method, comprising:
acquiring image data from an image detector, said image detector comprising a gamma ray radiation detector, said image data providing pixels in a two-dimensional imaging surface;
determining an exposure duration for one or more images;
processing said acquired image data into an image for display based on said determined exposure duration;
displaying said image;
wherein said determining an exposure duration comprises:
determining whether motion exists; and
based on said determining whether motion exists, increasing or decreasing the exposure duration;
wherein said determining comprises:
obtaining a plurality of sequential frames from said acquired image data having a time duration shorter than the image exposure duration; and
determining whether motion is present between two or more of the sequential frames;
wherein said processing said acquired image data into one or more images based on said determined exposure duration comprises:
if motion is determined, outputting a first exposure duration;
if motion is not determined, outputting a second exposure duration greater than said first exposure duration; and
temporally smoothing said obtained plurality of sequential images based on one of said output first and second exposure duration.

14. The method of claim 13, wherein said determining uses said acquired image data.

15. The method of claim 13, wherein said determining whether motion is present between two or more of the sequential frames comprises:
deriving a velocity vector for each of a plurality of pixels in the two or more sequential frames;
based on said derived velocity vectors, determining a correlated frame velocity magnitude.

16. The method of claim 15, further comprising:
comparing said correlated frame velocity magnitude to a threshold.

17. The method of claim 13, wherein before said determining whether motion is present, a time duration between said obtained plurality of sequential frames is smaller than said first exposure duration and said second exposure duration.

18. An imaging device, comprising:
an image detector configured to produce event data, said image detector comprising a gamma ray radiation detector;
a processor for converting the received event data into an image for display; and
a display for displaying said image;
wherein said processor is configured to:
acquire event data from said image detector to provide pixels in a two-dimensional imaging surface;
determine an exposure duration for one or more images; and process said acquired event data into the image based on said determined exposure duration;
wherein determining an exposure duration comprises:
  determining whether motion exists;
  based on said determining, decreasing the exposure duration by one of a first fixed amount and an amount proportional to an amount of image motion or increasing the exposure duration by one of a second fixed amount and an amount proportional to an amount of image motion;
  wherein said first fixed amount is greater than said second fixed amount.

19. The imaging device of claim 18, wherein the imaging device is a handheld device.

* * * * *